(12) United States Patent
Ozturk et al.

(10) Patent No.: US 10,000,513 B2
(45) Date of Patent: Jun. 19, 2018

(54) THIENOTHIOPHENE—BORON (DONOR-ACCEPTOR) BASED MATERIALS FOR ORGANIC LIGHT EMITTING DIODES

(71) Applicant: TUBITAK, Cankaya (TR)

(72) Inventors: Turan Ozturk, Istanbul (TR); Emine Tekin, Kocaeli (TR); Selin Piravadili Mucur, Kocaeli (TR); Ahmet Ceyhan Goren, Kocaeli (TR); Gulsen Turkoglu, Istanbul (TR); Mehmet Emin Cinar, Istanbul (TR); Ali Buyruk, Istanbul (TR)

(73) Assignee: TUBITAK, Ankara (TR)

( * ) Notice: Subject to any disclaimer, the term of this patent is extended or adjusted under 35 U.S.C. 154(b) by 0 days. days.

(21) Appl. No.: 15/552,492

(22) PCT Filed: Feb. 20, 2015

(86) PCT No.: PCT/IB2015/051306
§ 371 (c)(1),
(2) Date: Aug. 21, 2017

(87) PCT Pub. No.: WO2016/132180
PCT Pub. Date: Aug. 25, 2016

(65) Prior Publication Data
US 2018/0030069 A1    Feb. 1, 2018

(51) Int. Cl.
*C07F 5/02* (2006.01)
*H01L 51/00* (2006.01)
*C09K 11/06* (2006.01)
*H01L 51/50* (2006.01)

(52) U.S. Cl.
CPC .............. *C07F 5/025* (2013.01); *C09K 11/06* (2013.01); *H01L 51/0061* (2013.01); *C09K 2211/1018* (2013.01); *H01L 51/0003* (2013.01); *H01L 51/0074* (2013.01); *H01L 51/5088* (2013.01)

(58) Field of Classification Search
CPC ...................................................... C07F 5/025
USPC ............................................................ 549/4
See application file for complete search history.

(56) References Cited

PUBLICATIONS

Della Sala, F. et al: "The effects of oxygen and boron functionalization on the optical properties of dithienothiophenes", JNCSBJ, vol. 352, No. 23-25, Jun. 5, 2006 (Jun. 5, 2006), pp. 2461-2464, XP028046161, ISSN: 0022-3093, DOI: 10.1016/j.jnoncrysol.2006.02.081.

Mazzeo, Marco et al: "Bright white organic light-emitting devices from a single active molecular material", Advanced Materials, vol. 17, No. 1, Jan. 6, 2005 (Jan. 6, 2005), pp. 34-39, XP055094168, ISSN: 0935-9648, DOI: 10.1002/adma.200400670.

Poon, Chun-Ting et al: "Photochromic Dithienylethene-Containing Triarylborane Derivatives: Facile Approach to Modulate Photochromic Properties with Multi-addressable Functions", Chemistry—A European Journal, vol. 21, No. 5, Dec. 2, 2014 (Dec. 2, 2014), pp. 2182-2192, XP002739089, ISSN: 0947-6539, DOI: 10.1002/chem.20140478.

*Primary Examiner* — Taofiq A Solola
(74) *Attorney, Agent, or Firm* — Aeon Law, PLLC; Adam L. K. Philipp; Manasi Vakil

(57) ABSTRACT

The present invention discloses new molecules having defined structures of a series of thienothiophene (TT) and boron derivatives, light emitting devices of which are expected to be applied to organic light emitting diodes (OLED).

3 Claims, 2 Drawing Sheets

THIENOTHIOPHENE—BORON (DONOR-ACCEPTOR) BASED MATERIALS FOR ORGANIC LIGHT EMITTING DIODES

FIELD OF INVENTION

The present invention relates to thienothiophene and boron derivatives with specified structures. They have potential of application to organic light emitting diodes (OLED).

BACKGROUND OF THE INVENTION

Organic electronic and optoelectronic materials have the attention of growing number of, particularly, physics and chemistry researchers for more than 50 years, the main mason of which is the higher possibility of modifying the chemical structures of the organic compounds. Thus, the properties of the materials could directly be affected. Until the mid-1980s, stability and performance of the devices made of organic materials fell short of those devices based on materials such as silicon or gallium arsenide. This has been changed with the appearance of a low voltage and efficient thin film light emitting diode. It provided the possibility of using organic thin films for a new generation of electronic and optoelectronic devices. It has now been proven that organic thin films are useful in various applications and organic light emitting device (OLED) is the most successful one, which is used now in full-color displays.

Generally, two groups of organic materials, small molecules and polymers, are used in electronic and optoelectronic devices and both can be processed from solutions and allow low cost fabrication of devices. Small molecule and polymer electro-luminescent devices are described, for example, C. W. Tang, Appl. Phys. Letters, 1987, 51, 913-915; J. H. Burroughes, Nature, 1990, 347, 539; U.S. Pat. No. 6,727,008, U.S. Pat. No. 7,133,032, WO 2007/134280A1; US2005/01184A1; WO90/13148; US005399502; U.S. Pat. No. 4,356,429.

Designing high performance optical and electronic organic devices requires understanding of their electronic structures, and even some small tunings in the structure or composition of an organic material can alter its original properties enormously. Modification of the structures of the conjugated organic materials to tune their optoelectronic properties is a challenging topic. Thiophene-based organic materials are among the most promising compounds with tunable functional properties by proper molecular engineering. For example, converting oligothophenes into the corresponding oligothiophene-S,S-dioxides has been shown to be useful for increasing both thin film photoluminescence efficiencies and molecular energy levels.

Recently, boron has been applied to alter the properties of organic electronic and optoelectronic materials, which gave interesting results. Presence of empty $p_z$ orbital of boron, which behaves as strong electron withdrawing atom when it makes three bonds, is the main reason for altering the properties. It delocalizes electrons strongly when it is integrated to "π" systems, and conjugated organoboranes are now considered as new class of organic materials with their widespread applications in electronics, optoelectronics and sensors.

Materials, having the combinations of different functional building blocks like thiophene, thiophene derivatives and boron, tend to emit bright white light from a single active molecular material (M. Mazzeo, Adv. Mater. 2005, 17, 34). The AIE (Aggregation-Induced Emission) nature and hole-transport capability of a material, comprised of tetraphenylethylene and triphenylamine, have enabled the fabrication of OLEDs devices with simple structures and low-cost but good performance (Tang Z. B. Adv. Mater. 2010, 22, 19). AIE-Active materials incorporated with an inherently electron-deficient group, dimesitylboryl, enable them to serve simultaneously as bifunctional materials of light emitter and electron transporting layer in OLEDs (Tang Z. B. Adv. Functional Mater. 2014, 24, 3611-3630). Thus, it would be desirable developing materials having thiophene, thiophene derivatives and boron to obtain various emissions for organic light emitting diodes.

DISCLOSURE OF THE INVENTION

The invention discloses the compounds that are useful when employed as organic light emitting materials, i. e. organic light emitting diodes (OLED). They have potential of being employed as charge transport materials in electronic devices such as organic field effect transistors (OFET), organic photovoltaic diodes and the like. The invention discloses the compounds having the formulas (I).

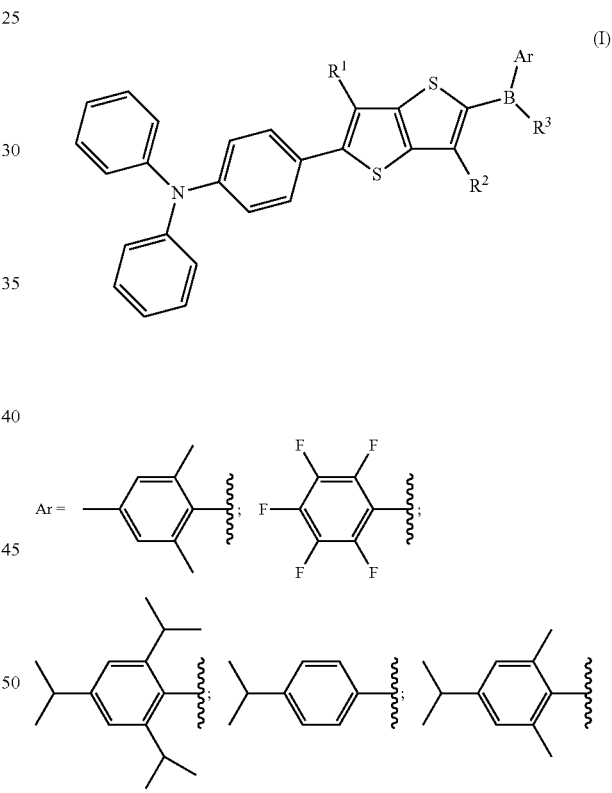

wherein
$R^1$, $R^2$ and $R^3$ are independently or equally atom chain(s)/group(s) of about 1 atom to 100 atoms. They may equally or independently have one or more of a group comprising branched or non-branched alkyl, aryl, alkenyl, alkynyl, amine, ester, carbonate ester, carbonyl, sulphide, organosilane and thiolate.

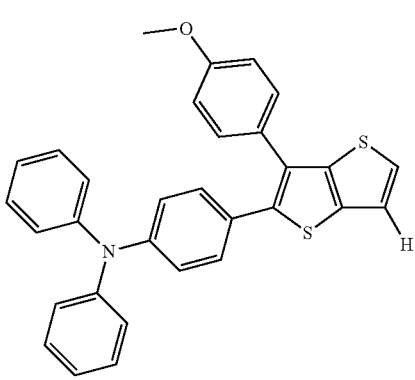

(II)

Thienothiophenes I (TT) was synthesized following the literature procedure (T. Ozturk, et al. *Tetrahedron,* 2005, 61, 11055; E. Ertas, et al. *Tetrahedron Lett.* 2004, 45, 3405; I. Osken, *Tetrahedron,* 2012, 68, 1216; P. Dundar, Synth. Met. 2012, 162, 1010; I. Osken, Thin Solid Films, 2011, 519, 7707; O. Sahin, Synth. Met. 2011, 161, 183; O. Mert, *J. Electroanal. Chem.* 2006, 591, 53; A. Capan, *Macromolecules* 2012, 45, 8228; I. Osken, *Macromolecules* 2013, 46, 9202). The TTs I were produced by lithiation of bromo-TTs II with n-BuLi, which was followed by addition of aryldimethoxyborane.

EXAMPLE

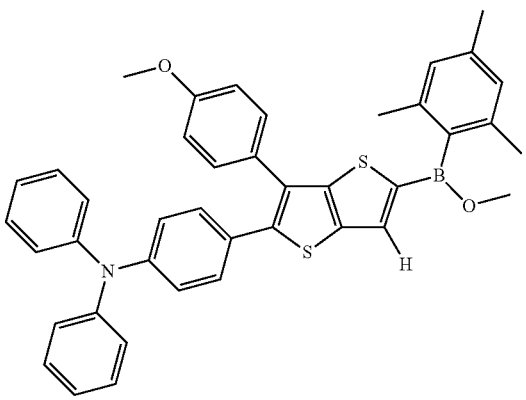

(I)

A Procedure for the Synthesis of 4-(5-(mesityl (methoxy)boranyl)-3-(4-methoxyphenyl)thieno[3,2-b]thiophen-2-yl)-N,N-diphenylaniline (I*)

To a solution of 4-(3-(4-methoxyphenyl)thieno[3,2-b]thiophen-2-yl)-N,N-diphenylaniline (123 mg, 240 μmol) in 30 mL of dry THF was added n-BuLi (185 μL, 290 μmol) dropwise at −78° C. under nitrogen atmosphere. The reaction mixture was stirred at same temperature for 1 h. Then MesB(OMe)$_2$ (51.0 μL, 240 μmol) was added at −78° C. and the solution was heated slowly up to room temperature and then stirred for another 12 h. The product was extracted with dichloromethane (3×20 mL). The solution was washed with brine and H$_2$O, and then dried over NaSO$_4$. After removal of the solvent under atmospheric, the crude product was purified by column chromatography over silica gel using a mixture of n-hexane/dichloromethane (6:1) as eluent. The product was obtained as a green solid in 45% yield; R$_f$=0.85; M.p. 179-180° C.; $^1$H NMR (500 MHz, CDCl$_3$) δ 7.74 (s, 1H), 7.38 (d, J=9.0 Hz, 2H), 7.26 (t, J=8.0 Hz, 4H), 7.18 (d, J=9.0 Hz, 2H), 7.11 (d, J=7.5 Hz, 4H), 7.05 (t, J=7.5 Hz, 2H), 6.92 (dd, J=8.0, 2.5 Hz 4H), 6.82 (s, 2H), 3.83 (s, 3H), 2.32 (s, 3H), 2.10 ppm (s, 6H); $^{13}$C NMR (125 MHz, CDCl$_3$): δ 158.9, 152.5, 147.6, 1472, 146.7, 144.3, 137.6, 136.6, 136.5, 132.5, 131.5, 130.2, 129.8, 129.4, 129.3, 127.8, 127.6, 126.9, 124.9, 123.4, 122.1, 114.2, 55.2, 28.1, 22.3 ppm.

Example of a Device Fabrication:

Organic light emitting devices were fabricated by coating the molecules from their solution onto electrically conductive substrates. The molecule (I) was dissolved in a mixture of toluene/dichlorobenzene (8 mg/ml). Indium thin oxide (ITO), coated (15 ohms/sq.) on a glass, was employed as an anode electrode. PEDOT:PSS, as a hole injection layer, was spin-coated on ITO, which was dried at 110° C. for 10 min. Subsequently, molecule film, as an active layer, was coated by spin coating. Finally, LiF (1 nm) and aluminum (Al, 100 nm) was deposited under vacuum (~10$^{-6}$ mbar) by thermal evaporation technique to assemble the cathode electrodes.

Figure 1:
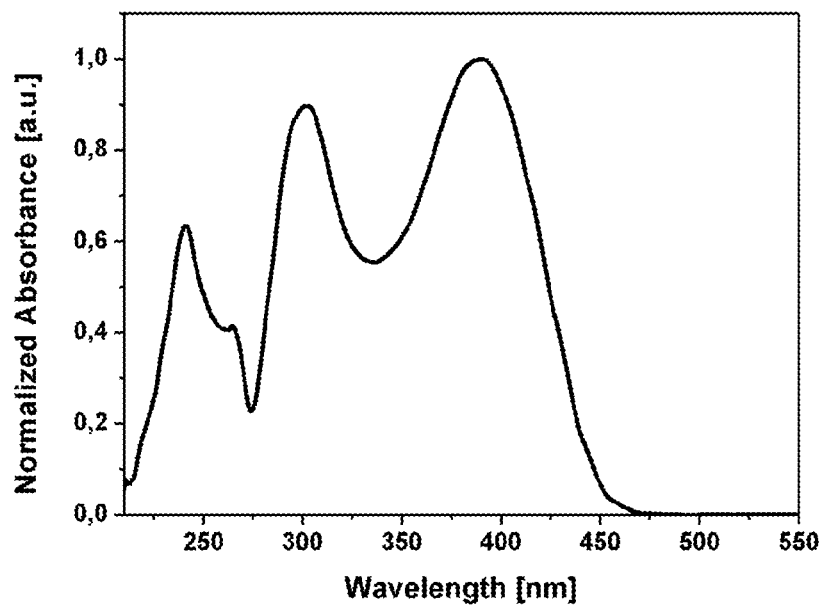
FIG. 1. UV-Vis spectrum of molecule (I) in tetrahydrofuran (THF) solution at room temperature FIG. 2. Fluorescence spectrums of molecule (I) in tetrahydrofuran solution (THF) and in the solid state (on ITO coated glass) at room temperature FIG. 3. a) Electroluminescent spectrum of the fabricated device of the molecule (I) (device layout: PEDOT/Molecule (I*)/LiF/Al), b) CIE coordinates of the fabricated device of the molecule (I) at different voltages. The electroluminescent spectrum covers the region almost from 400 nm to 650 nm. Color coordinates are in the region for blue-green color according to the CIE 1931 Chromaticity Diagram.
Figure 2:
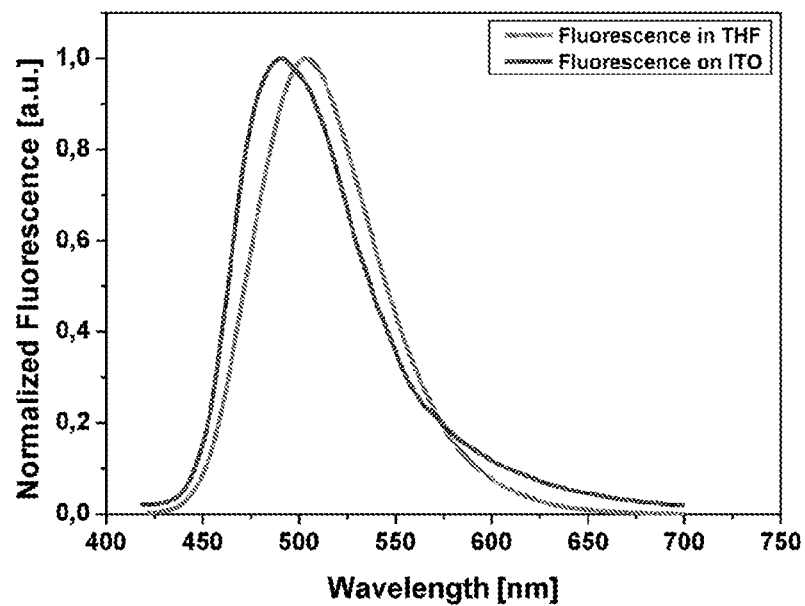
Figure 3:
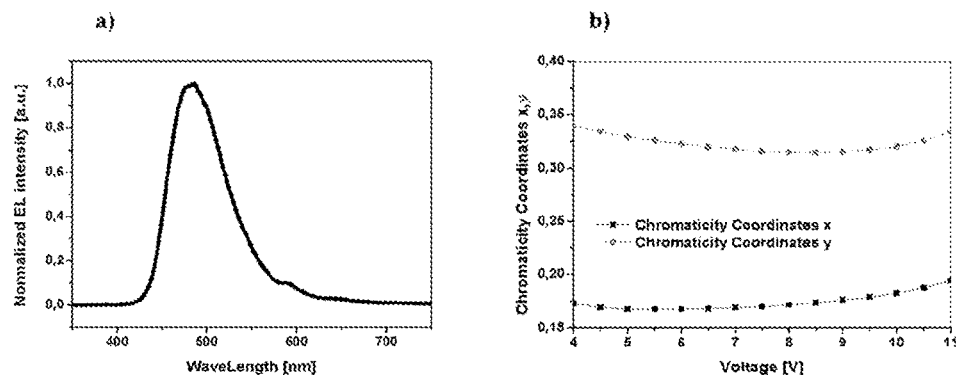
Figure 4:
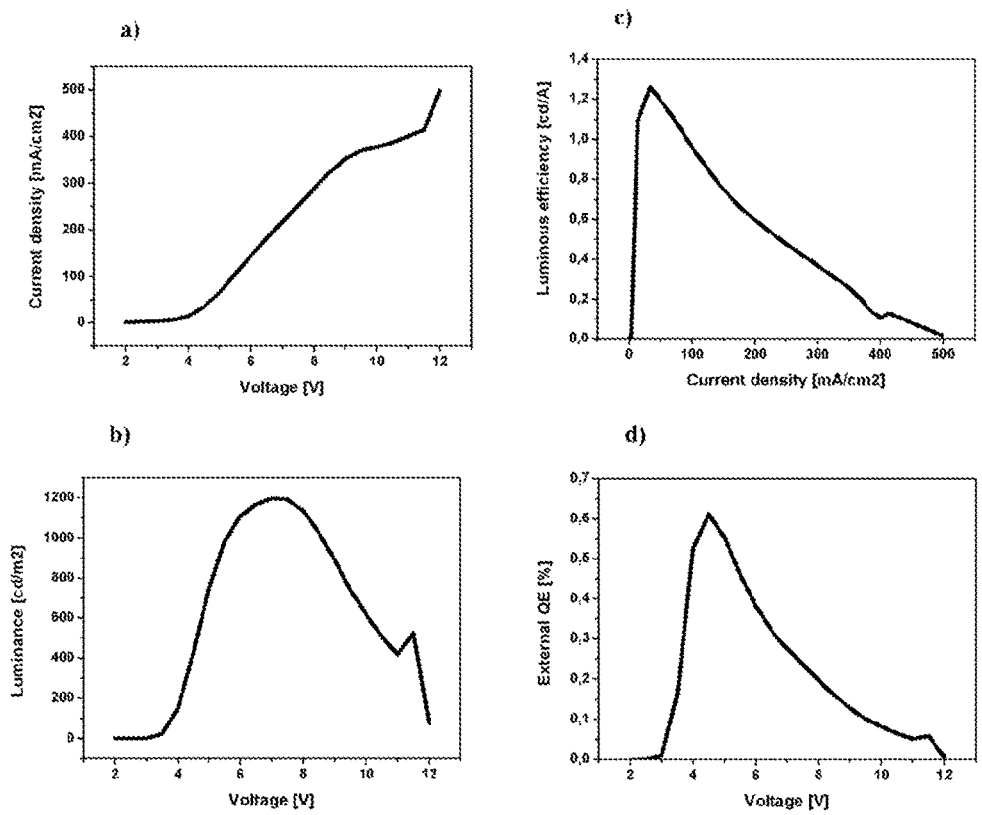
FIG. 4. OLED device characteristics: a) voltage-current b) luminance-voltage c) luminous efficiency-current density and d) external quantum efficiency-current density.

We claim:

1. Compound of formula (I)

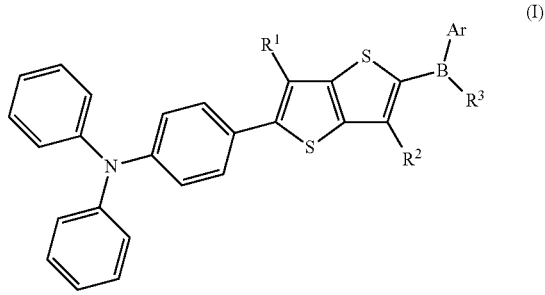

(I)

-continued

Ar = 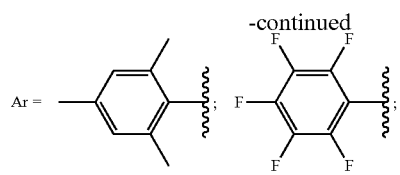

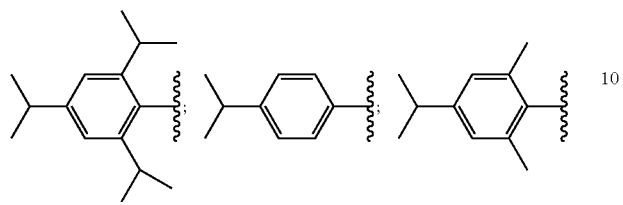

wherein

R$^1$, R$^2$ and R$^3$ are independently or equally atom chain(s)/group(s) of about 1 atom to 100 atoms equally or independently have one or more of a group comprising branched or non-branched alkyl, aryl, alkenyl, alkynyl, amine, ester, carbonate ester, carbonyl, sulphide, organosilane and thiolate.

2. Formulation comprising the compounds given in claim 1.

3. A method of using the formulation comprising the compound given in claim 1 as charge transport, electrically conducting, semiconducting, photoconducting or light emitting material in electronic, optical, electrooptical, electroluminescent or photoluminescent components or devices.

* * * * *